United States Patent [19]

Tsuk

[11] Patent Number: 4,627,429
[45] Date of Patent: Dec. 9, 1986

[54] STORAGE-STABLE TRANSDERMAL ADHESIVE PATCH

[75] Inventor: Andrew G. Tsuk, Clinton, N.Y.

[73] Assignee: American Home Products Corporation, New York, N.Y.

[21] Appl. No.: 834,255

[22] Filed: Feb. 28, 1986

[51] Int. Cl.4 .............................................. A61L 15/00
[52] U.S. Cl. .................................................... 128/156
[58] Field of Search ............... 128/156, 268, 260, 155; 206/441

[56] References Cited

U.S. PATENT DOCUMENTS 3,897,780  8/1975  Trousil ................................. 128/156
4,265,234  5/1981  Schaar ................................. 128/156
4,341,208  7/1982  Gordon ............................... 128/156

Primary Examiner—Gregory E. McNeill
Attorney, Agent, or Firm—John W. Routh

[57] ABSTRACT

A storage-stable transdermal adhesive bandage structure having incorporated within a medicinal impregnated matrix which when applied to the skin provides an elegant clear or colored plastic patch type dosage form.

1 Claim, 6 Drawing Figures

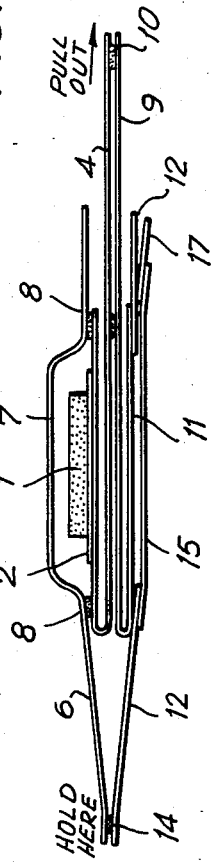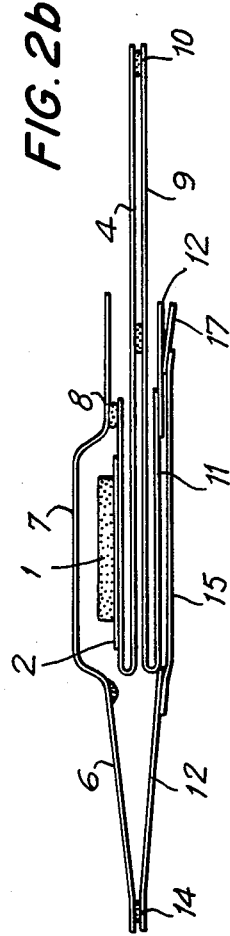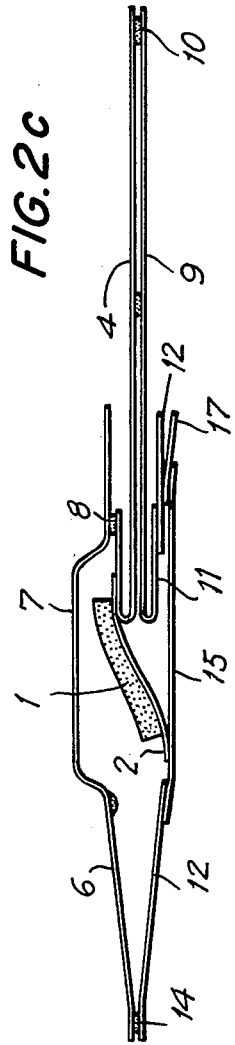

STORAGE-STABLE TRANSDERMAL ADHESIVE PATCH

BACKGROUND OF THE INVENTION

This invention relates to a storage-stable transdermal adhesive bandage structure for the administration of medicinal substances by means of a patch through the skin of patients.

Medicinal formulations in transdermal dosage forms (patches) must be sealed in a vapor tight manner for storage, if they need protection from air or moisture, or if they contain volatile ingredients. In the latter case, the seal must also isolate the formulation from the adhesive which is meant to secure the patch to the skin. The vapor tight seal in all commercial patches consists of sheets of aluminum foil film laminates, because plastic films without aluminum foil are not sufficiently impermeable to vapors. Typically, the formulation is enclosed between two sheets of such aluminum foil laminates, heat-sealed together. One of these sheets then remains on the patch which is worn by the patient. Aluminum foil worn in transdermal patches has drawbacks: it renders the patch opaque and esthetically unpleasing, it presents a hazard when exposed to high electric potentials or microwave radiation, and it has caused skin irritation.

It is the object of the invention to construct a transdermal dosage form, where the formulation portion is completely sealed between sheets of aluminum foil film laminates during storage, but contains no aluminum foil in the patch when worn by the patient.

SUMMARY OF THE INVENTION

This invention comprises a storage-stable transdermal adhesive structure composed of seven separate components which, when assembled, provide a storage-stable bandage structure but when applied to the skin also provides an elegant clear or colored plastic patch type dosage form containing a medicinal impregnated matrix for transdermal administration of a medicament from the matrix.

The seven components comprise:

(a) a first pull tab having an upper surface and a heat-sealable film laminate lower surface and being folded over such that a portion of the lower surface is upwardly facing, said pull tab having disposed on the upwardly facing lower surface;

(b) a matrix having a medicinal formulation incorporated therein said matrix being smaller in area than the upwardly facing lower surface of the pull tab;

(c) an occlusive film adhesively bonded to the matrix and situated between the upwardly facing lower surface of the pull tab and the lower surface of the matrix, said film extending outwardly from the periphery of the matrix;

(d) a cover having a heat-sealable film laminate lower surface covering the occlusive film and being heat-sealably bonded to the heat-sealable upwardly facing lower surface of the pull tab surrounding the occlusive film;

(e) a second pull tab having an upper adhesive release surface folded under such that the upwardly facing adhesive release surface is coextensive with the lower surface of the first pull tab, said first and second pull tabs being fastened together at the extremity opposite the fold;

(f) a release liner having upper and lower surfaces coextensive with the cover and being fastened along its periphery to the cover, the release liner having an opening therein larger in area than the occlusive film covering the matrix;

(g) a non-occlusive adhesive film covering the opening in the release liner and extending outwardly from the periphery of the opening, and said peripherally extending film portion being adhesively bonded to the lower surface of the release liner.

DETAILED DESCRIPTION OF THE INVENTION

The transdermal structure of the invention is now described with reference to FIGS. 1 and 2 of the accompanying drawings wherein.

Figure 1:
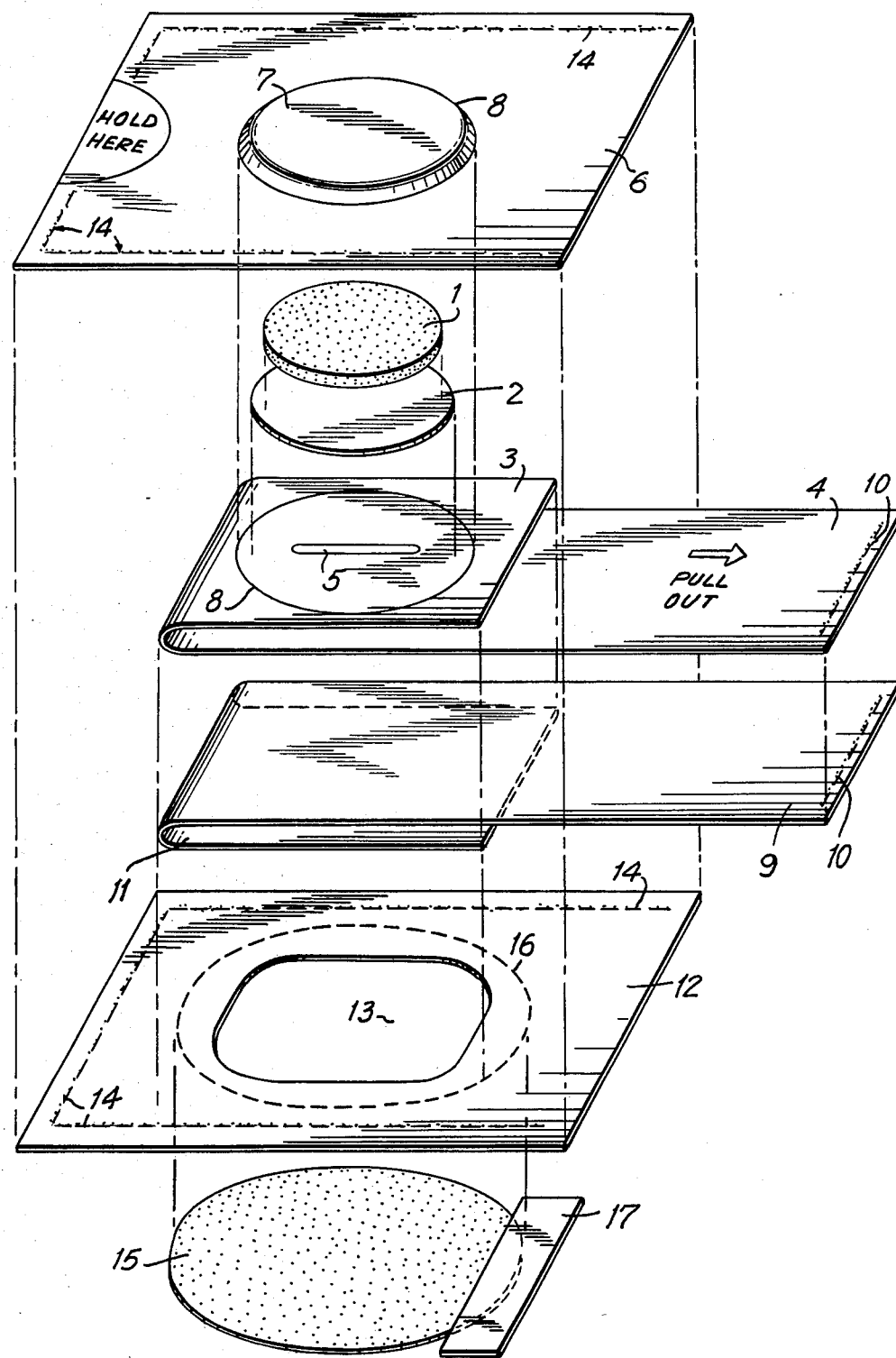
FIG. 1 is an exploded view of the transdermal structure of the invention showing the seven separate parts and their relationship one to the other when assembled.

Turning now to FIG. 1, the medicinal formulation is contained in matrix 1. In one embodiment, this is a liquid drug formulation contained in an oval piece of open-cell polyurethane foam sheet, approximately 0.8 mm thick. The foam holds the liquid formulation in the manner of a sponge. Matrix 1 is adhesively bonded to occlusive film 2, whose shape is similar to the matrix, but is of slightly larger size. The occlusive film is of matte-finish polyethylene, and its role is to cover the matrix containing the liquid formulation when on the skin, to prevent seapage of liquid from the treated skin, and to increase moisture retention on the treated skin. Occlusive film 2 rests on the folded-back portion 3 of pull-strip 4, which is made of a heat-sealable aluminum foil film laminate, the heat-sealable surface being the upper side of portion 3. An optional line 5 (or string of dots) of pressure sensitive adhesive secures film 2 to strip 3. Cover 6 is also made of a heat-sealable aluminum foil film laminate, heat-sealable surface down, as shown on FIG. 1. A formed cup or dome 7 in cover 6 allows room for matrix 1 and occlusive film 2. Cover 6 and portion 3 of pull-strip 4 are heat-sealed together along oval line 8. Another pull-strip 9 is attached to pull-strip 4 along glue-line 10. Pull-strip 9 is made of release liner material, such as light-weight paper treated on one surface to allow separation from pressure sensitive adhesives. The release surface of strip 9 is the upper side, and portion 11 of strip 9 is folded under as shown on the figure. Release liner 12 has the shape and size of cover 6, and can be made of heavy-weight paper, with its treated release surface down, as shown on FIG. 1. Release liner 12 has a hole 13 cut out, and this hole is larger than occlusive film 2, but is completely covered by portion 11 of pull-strip 9. Release liner 12 is attached to cover 6 along glue-lines 14. Non-occlusive adhesive film 15 is larger than hole 13, and is of oval, or other suitable shape. Outline 16 shows the edge of film 15 as it adheres to the underside of liner 12. The role of the non-occlusive adhesive film is to provide an adhesive margin around the matrix, to secure it to the skin. Porous adhesive-coated nonwoven fabrics allow moisture to leave the skin from under the adhesive margin, and are preferred materials for this purpose. The adhesive side of film 15 is up, as shown on the figure. Tab 17 helps the patient remove the patch for application, and is made of release liner material the same as liner 12, with its release surface down as shown in FIG. 1.

Figure 2D:
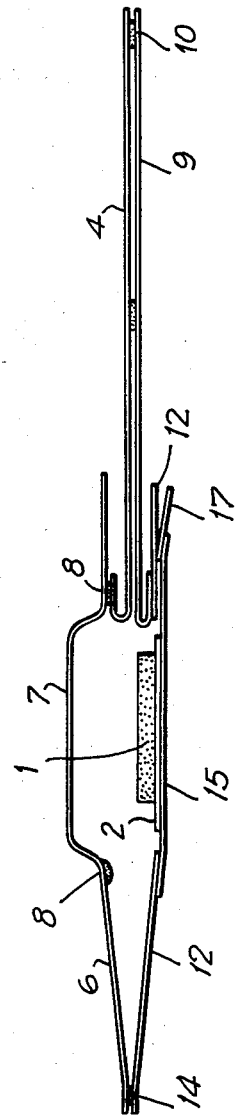
FIG. 2 is a series of views showing five different stages of the transdermal structure as it is being opened to release the patch containing the matrix impregnated with the medicament. In both figures, the first and second pull tabs numbered 4 and 9 permit fulfillment of the objective of the invention.
Figure 2E:
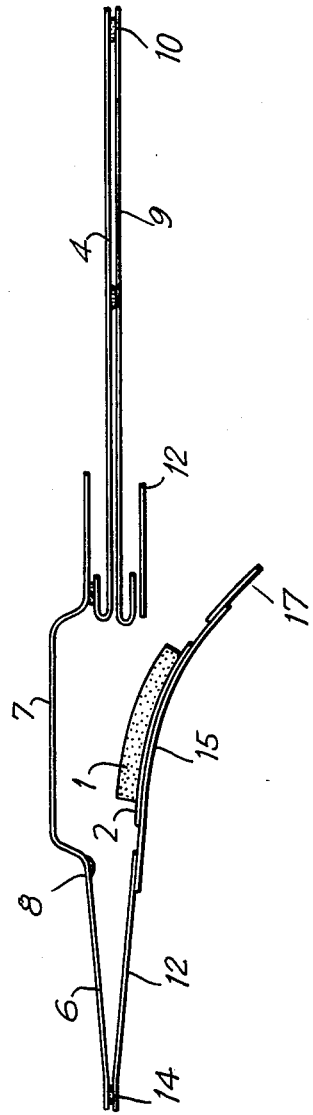

Turning to FIG. 2., sketch 2a. shows a cross section of the sealed dosage form, and the numbered parts are as identified in FIG. 1. As the pull-strips are pulled out, the heat-sealed oval line 8 is peeled apart, as shown on sketch 2b. At the same time, a portion of the adhesive surface of non-occlusive film 15 becomes exposed. In sketch 2c., the combination of matrix 1 and occlusive film 2 is dropping onto the adhesive surface of non-occlusive film 15. This process is completed in sketch 2d. Finally, as shown in sketch 2e., the patient peels away a complete transdermal patch for application. The patch is composed of matrix 1, occlusive film 2, and non-occlusive film 15, none of which contain any aluminum foil.

I claim:

1. A storage-stable transdermal adhesive bandage structure comprising:
    (a) a first pull tab having an upper surface and a heat-sealable film laminate lower surface and being folded over such that a portion of the lower surface is upwardly facing, said pull tab having disposed on the upwardly facing lower surface;
    (b) a matrix having a medicinal formulation incorporated therein said matrix being small in area than the upwardly facing lower surface of the pull tab;
    (c) an occlusive film adhesively bonded to the matrix and situated between the upwardly facing lower surface of the pull tab and the lower surface of the matrix, said film extending outwardly from the periphery of the matrix;
    (d) a cover having a heat-sealable film laminate lower surface covering the occlusive film and being heat-sealably bonded to the heat-sealable upwardly facing lower surface of the pull tab surrounding the occlusive film;
    (e) a second pull tab having an upper adhesive release surface folded under such that the upwardly facing adhesive release surface is coextensive with the lower surface of the first pull tab, said first and second pull tabs being fastened together at the extremity opposite the fold;
    (f) a release liner having upper and lower surfaces coextensive with the cover and being fastened along its periphery to the cover, the release liner having an ipening therein larger in area than the occlusive film covering the matrix;
    (g) a non-occlusive adhesive film covering the opening in the release liner and extending outwardly from the periphery of the opening, and said peripherally extending film portion being adhesively bonded to the lower surface of the release liner.

* * * * *